US012304980B2

United States Patent
Masere et al.

(10) Patent No.: US 12,304,980 B2
(45) Date of Patent: May 20, 2025

(54) ANTIFOULANT COMPOSITIONS FOR VAPOR-SPACE APPLICATIONS

(71) Applicant: ECOLAB USA INC., St. Paul, MN (US)

(72) Inventors: Jonathan Masere, Richmond, TX (US); Zhenxing Xi, Katy, TX (US); David Dixon, Baton Rouge, LA (US); Gregory Appel Melancon, Jr., Baton Rouge, LA (US); Ramon Colorado, Jr., Stafford, TX (US); Peter Webber, Sugar Land, TX (US)

(73) Assignee: Ecolab USA Inc., St. Paul, MN (US)

( * ) Notice: Subject to any disclaimer, the term of this patent is extended or adjusted under 35 U.S.C. 154(b) by 83 days.

(21) Appl. No.: 18/191,262

(22) Filed: Mar. 28, 2023

(65) Prior Publication Data
US 2023/0312770 A1    Oct. 5, 2023

Related U.S. Application Data

(60) Provisional application No. 63/326,389, filed on Apr. 1, 2022.

(51) Int. Cl.
C08F 2/40    (2006.01)

(52) U.S. Cl.
CPC ..................... C08F 2/40 (2013.01)

(58) Field of Classification Search
CPC . C08F 2/40; C07C 51/50; C07C 67/62; C07C 7/20; C07C 211/51; C07C 11/167;
(Continued)

(56) References Cited

U.S. PATENT DOCUMENTS

| 2,344,346 A | 3/1944 | Harry |
| 2,642,410 A | 6/1953 | Hoppens |

(Continued)

FOREIGN PATENT DOCUMENTS

| CN | 101304944 A | 11/2008 |
| CN | 102249842 A | 11/2011 |

(Continued)

OTHER PUBLICATIONS

Georgieff, K. K. (1965). Relative inhibitory effect of various compounds on the rate of polymerization of methyl methacrylate. Journal of Applied Polymer Science, 9(6), 2009-2018. doi:10.1002/app.1965.070090602.

(Continued)

*Primary Examiner* — Prem C Singh
*Assistant Examiner* — Francis C Campanell
(74) *Attorney, Agent, or Firm* — Eric D. Babych; Barnes & Thornburg LLP

(57) ABSTRACT

Polymerization inhibitor compositions are provided. The polymerization inhibitor compositions include at least a first inhibitor compound including a hydroxylamine, a second inhibitor including phenylenediamine, and a third inhibitor including a benzoquinone or naphthoquinone. Methods of inhibiting the polymerization of monomers using the compositions of the disclosure are also provided. The methods of inhibiting polymerization of monomers include a step of adding a composition of the disclosure to the monomer. In some instances, the monomer is an ethylenically unsaturated monomer. Such ethylenically unsaturated monomers include, but are not limited to, vinyl acetate, acrylonitrile, acrylates, methacrylates, 1,3-butadiene, styrene, isoprene, (meth)acrylic acid, and combinations thereof. Methods of preparing the polymerization inhibitors and compositions of the disclosure are also provided.

19 Claims, 1 Drawing Sheet

(58) Field of Classification Search
CPC ......... C07C 11/18; C07C 13/15; C07C 15/46; C07C 57/04; C07C 69/15; C07D 221/00
USPC .............................................. 523/305; 585/4
See application file for complete search history.

(56) References Cited

U.S. PATENT DOCUMENTS

| | | | |
|---|---|---|---|
| 3,445,312 A | 5/1969 | Rider | |
| 3,632,564 A | 1/1972 | Albert et al. | |
| 3,697,470 A | 10/1972 | Haines et al. | |
| 3,816,077 A | 6/1974 | Rosen et al. | |
| 4,079,123 A | 3/1978 | Fuller et al. | |
| 4,216,195 A | 8/1980 | Jaszka et al. | |
| 4,393,035 A | 7/1983 | Fredette | |
| 4,735,744 A | 4/1988 | Tsujimoto et al. | |
| 4,912,247 A | 3/1990 | Roling | |
| 5,221,764 A | 6/1993 | Roling | |
| 5,254,760 A | 10/1993 | Winter et al. | |
| 5,258,138 A | 11/1993 | Gatechair et al. | |
| 5,272,231 A | 12/1993 | Campbell et al. | |
| 5,296,567 A | 3/1994 | Baumann et al. | |
| 5,322,960 A | 6/1994 | Sakamoto et al. | |
| 5,324,497 A | 6/1994 | Westerlund | |
| 5,374,697 A | 12/1994 | Muller | |
| 5,396,004 A | 3/1995 | Arhancet et al. | |
| 5,710,329 A | 1/1998 | Clever | |
| 5,728,872 A | 3/1998 | Riemenschneider | |
| 5,856,562 A | 1/1999 | Mine et al. | |
| 5,877,344 A | 3/1999 | Gande et al. | |
| 5,888,356 A | 3/1999 | Keil et al. | |
| 5,910,232 A | 6/1999 | Hyde et al. | |
| 5,955,643 A | 9/1999 | Lewis | |
| 6,051,135 A | 4/2000 | Lee et al. | |
| 6,210,536 B1 | 4/2001 | Grossi et al. | |
| 6,287,483 B1 | 9/2001 | DeMassa et al. | |
| 6,300,513 B2 | 10/2001 | Sakamoto et al. | |
| 6,300,533 B1 | 10/2001 | Benage et al. | |
| 6,337,426 B1 | 1/2002 | Winter | |
| 6,342,647 B1 | 1/2002 | Roof et al. | |
| 6,344,560 B1 | 2/2002 | Geelan et al. | |
| 6,348,598 B1 | 2/2002 | Doi et al. | |
| 6,352,619 B1 | 3/2002 | Fauconet et al. | |
| 6,403,850 B1 | 6/2002 | Benage et al. | |
| 6,409,887 B1 | 6/2002 | Pryce et al. | |
| 6,518,374 B1 | 2/2003 | Aichinger et al. | |
| 6,518,452 B1 | 2/2003 | Aichinger et al. | |
| 6,608,226 B1 | 8/2003 | Reid et al. | |
| 6,642,337 B1 | 11/2003 | Misiak et al. | |
| 6,660,181 B2 | 12/2003 | Benage et al. | |
| 6,770,219 B2 | 8/2004 | Tong | |
| 6,790,427 B2 | 9/2004 | Charles et al. | |
| 6,806,385 B1 | 10/2004 | Hammon et al. | |
| 6,864,313 B2 | 3/2005 | Wunderlich et al. | |
| 6,956,130 B2 | 10/2005 | Riondel et al. | |
| 7,005,087 B2 | 2/2006 | Tong | |
| 7,022,220 B2 | 4/2006 | Benage et al. | |
| 7,041,711 B2 | 5/2006 | Kunita | |
| 7,056,642 B2 | 6/2006 | Kano et al. | |
| 7,119,224 B2 | 10/2006 | Schroeder et al. | |
| 7,261,821 B2 | 8/2007 | Beardwood | |
| 7,368,594 B2 | 5/2008 | Yurugi et al. | |
| 7,414,162 B2 | 8/2008 | Link et al. | |
| 7,420,013 B2 | 9/2008 | Riegel et al. | |
| 7,504,074 B2 | 3/2009 | Martens et al. | |
| 7,553,896 B2 | 6/2009 | Ma et al. | |
| 7,621,821 B2 | 11/2009 | Tsai et al. | |
| 7,682,592 B2 | 3/2010 | Charles et al. | |
| 7,799,198 B2 | 9/2010 | Nanjundiah et al. | |
| 8,691,994 B2 | 4/2014 | Tong | |
| 8,907,121 B2 | 12/2014 | Johnson et al. | |
| 9,133,288 B2 | 9/2015 | Loyns et al. | |
| 9,399,622 B2 | 7/2016 | Tong | |
| 9,534,065 B2 | 1/2017 | Nakaya et al. | |
| 9,561,997 B2 | 2/2017 | Dafinger et al. | |
| 9,573,874 B2 | 2/2017 | Fruchey et al. | |
| 9,611,336 B2 | 4/2017 | Mo et al. | |
| 9,656,891 B2 | 5/2017 | Martin | |
| 9,725,649 B2 | 8/2017 | Subramaniyam | |
| 9,783,480 B2 | 10/2017 | Aizawa et al. | |
| 9,884,795 B2 | 2/2018 | Mo et al. | |
| 9,884,951 B2 | 2/2018 | Tong | |
| 9,914,701 B2 | 3/2018 | Masere et al. | |
| 9,932,291 B2 | 4/2018 | Mendoza et al. | |
| 9,957,209 B2 | 5/2018 | Masere et al. | |
| 10,112,888 B2 | 10/2018 | Tong | |
| 10,221,255 B2 | 3/2019 | Marguerre et al. | |
| 10,308,585 B2 | 6/2019 | Tong | |
| 10,532,320 B2 | 1/2020 | Boam et al. | |
| 10,640,449 B2 | 5/2020 | Atkins et al. | |
| 10,696,618 B2 | 6/2020 | Tong | |
| 10,745,345 B2 | 8/2020 | Khanlari et al. | |
| 10,781,157 B2 | 9/2020 | Cabon et al. | |
| 10,869,444 B2 | 12/2020 | Masere et al. | |
| 11,104,626 B2 | 8/2021 | Masere et al. | |
| 11,174,439 B2 | 11/2021 | Vachon et al. | |
| 11,180,578 B2 | 11/2021 | Masere et al. | |
| 2001/0005755 A1 | 6/2001 | Sakamoto et al. | |
| 2001/0009929 A1 | 7/2001 | Blankenship et al. | |
| 2004/0031674 A1 | 2/2004 | Schroder | |
| 2004/0175322 A1 | 9/2004 | Woodruff et al. | |
| 2004/0236143 A1 | 11/2004 | Martan et al. | |
| 2005/0010065 A1 | 1/2005 | Wartini et al. | |
| 2005/0113626 A1* | 5/2005 | Benage ................ | C09K 15/04 208/48 AA |
| 2005/0139807 A1 | 6/2005 | Tong | |
| 2006/0051285 A1 | 3/2006 | Hawker et al. | |
| 2006/0096930 A1 | 5/2006 | Beardwood | |
| 2006/0120946 A1 | 6/2006 | Simic et al. | |
| 2006/0287548 A1 | 12/2006 | Hoefer et al. | |
| 2007/0116637 A1 | 5/2007 | Woodruff et al. | |
| 2007/0152187 A1 | 7/2007 | Truchlaeft | |
| 2007/0167650 A1 | 7/2007 | Ishikawa et al. | |
| 2008/0021241 A1 | 1/2008 | Carlson, Jr. et al. | |
| 2009/0203938 A1 | 8/2009 | Croizy et al. | |
| 2010/0168434 A1 | 7/2010 | Loyns et al. | |
| 2010/0219371 A1 | 9/2010 | Paul | |
| 2011/0015460 A1 | 1/2011 | Ding et al. | |
| 2011/0160484 A1 | 6/2011 | Fruchey et al. | |
| 2011/0290635 A1 | 12/2011 | Kar et al. | |
| 2012/0203020 A1 | 8/2012 | Tong | |
| 2012/0244063 A1 | 9/2012 | Pohjanvesi | |
| 2013/0178652 A1 | 7/2013 | Fruchey et al. | |
| 2013/0209349 A1 | 8/2013 | Vilhelmsson et al. | |
| 2014/0097095 A1 | 4/2014 | Moser | |
| 2014/0228604 A1 | 8/2014 | Colorado, Jr. et al. | |
| 2014/0302176 A1 | 10/2014 | Grund et al. | |
| 2015/0152053 A1 | 6/2015 | Tong | |
| 2016/0083323 A1 | 3/2016 | Fruchey et al. | |
| 2016/0102189 A1 | 4/2016 | Tong | |
| 2016/0122643 A1 | 5/2016 | Fruchey et al. | |
| 2018/0044180 A1 | 2/2018 | Burke et al. | |
| 2018/0057740 A1 | 3/2018 | Cavezzan et al. | |
| 2018/0264431 A1 | 9/2018 | Leeton et al. | |
| 2018/0265447 A1 | 9/2018 | Linemann et al. | |
| 2018/0273381 A1 | 9/2018 | Xiong et al. | |
| 2018/0361319 A1 | 12/2018 | Boam et al. | |
| 2019/0023641 A1 | 1/2019 | Chretien et al. | |
| 2019/0185769 A1 | 6/2019 | Cuoq et al. | |
| 2020/0017610 A1* | 1/2020 | Masere ................ | C08K 5/08 |
| 2020/0102408 A1 | 4/2020 | Masere | |
| 2020/0277249 A1 | 9/2020 | Dafinger et al. | |
| 2020/0283597 A1 | 9/2020 | Pelati | |
| 2020/0339880 A1 | 10/2020 | Masere et al. | |
| 2021/0108141 A1 | 4/2021 | Masere | |
| 2021/0380523 A1 | 12/2021 | Bellini et al. | |
| 2023/0312770 A1 | 10/2023 | Masere et al. | |

FOREIGN PATENT DOCUMENTS

| | | |
|---|---|---|
| CN | 103073375 A | 5/2013 |
| CN | 105482851 A | 4/2016 |
| CN | 106103340 A | 11/2016 |
| CN | 106554244 A | 4/2017 |
| CN | 107987888 A | 5/2018 |

(56) References Cited

FOREIGN PATENT DOCUMENTS

| | | |
|---|---|---|
| CN | 108191640 A | 6/2018 |
| CN | 106512879 B | 4/2019 |
| CN | 106588647 B | 4/2020 |
| CN | 112028770 A | 12/2020 |
| CN | 113024447 A | 6/2021 |
| CN | 113457571 A | 10/2021 |
| CZ | 294776 B6 | 3/2005 |
| EP | 0325059 A2 | 7/1989 |
| EP | 0697386 A1 | 2/1996 |
| EP | 0569502 B1 | 4/1996 |
| EP | 0791573 A1 | 8/1997 |
| EP | 0620206 B2 | 5/2000 |
| EP | 1077206 A1 | 2/2001 |
| EP | 0845448 B1 | 1/2002 |
| EP | 1694715 B1 | 10/2007 |
| EP | 1248757 B1 | 11/2007 |
| EP | 2017293 A1 | 1/2009 |
| EP | 2257519 B1 | 8/2011 |
| EP | 2066613 B1 | 6/2012 |
| EP | 2903961 B1 | 11/2016 |
| EP | 2670800 B1 | 1/2018 |
| EP | 2504308 B1 | 5/2021 |
| GB | 590680 A | 7/1947 |
| GB | 688206 A | 3/1953 |
| GB | 2093464 A | 9/1982 |
| JP | H1143449 A | 2/1999 |
| JP | 2000063371 A | 2/2000 |
| JP | 2000072718 A | 3/2000 |
| JP | 2001069429 A | 3/2001 |
| JP | 2001163831 A | 6/2001 |
| JP | 3187345 B2 | 7/2001 |
| JP | 3197947 B2 | 8/2001 |
| JP | 3227204 B2 | 11/2001 |
| JP | 3235980 B2 | 12/2001 |
| JP | 3312639 B2 | 8/2002 |
| JP | 3529613 B2 | 5/2004 |
| JP | 2006199736 A | 8/2006 |
| JP | 2006282541 A | 10/2006 |
| JP | 4225707 B2 | 2/2009 |
| JP | 4270821 B2 | 6/2009 |
| JP | 4520092 B2 | 8/2010 |
| JP | 4548821 B2 | 9/2010 |
| JP | 4548822 B2 | 9/2010 |
| JP | 4582641 B2 | 11/2010 |
| JP | 5191702 B2 | 5/2013 |
| JP | 5334390 B2 | 11/2013 |
| JP | 6032463 B2 | 11/2016 |
| JP | 6158044 B2 | 7/2017 |
| JP | 6705120 B2 | 6/2020 |
| JP | 2020200465 A | 12/2020 |
| SU | 957153 A1 | 9/1982 |
| WO | 1999007664 A1 | 2/1999 |
| WO | 1999055797 A1 | 11/1999 |
| WO | 2000031005 A1 | 6/2000 |
| WO | 2000037412 A1 | 6/2000 |
| WO | 2000064947 A1 | 11/2000 |
| WO | 2001040404 A1 | 6/2001 |
| WO | 2001047844 A1 | 7/2001 |
| WO | 2002051784 A1 | 7/2002 |
| WO | 2002094884 A2 | 11/2002 |
| WO | 2007063031 A2 | 6/2007 |
| WO | 2010094982 A1 | 8/2010 |
| WO | 2015140549 A1 | 9/2015 |
| WO | 2017041204 A1 | 3/2017 |
| WO | 2017081611 A1 | 5/2017 |
| WO | 2017091599 A1 | 6/2017 |
| WO | 2017187150 A1 | 11/2017 |
| WO | 2018164226 A1 | 9/2018 |
| WO | 2018221314 A1 | 12/2018 |
| WO | 2019142887 A1 | 7/2019 |
| WO | 2020038496 A2 | 2/2020 |
| WO | 2020183105 A1 | 9/2020 |
| WO | 2021022550 A1 | 2/2021 |

OTHER PUBLICATIONS

Li, R., & Schork, F. J. (2006). Modeling of the Inhibition Mechanism of Acrylic Acid Polymerization. Industrial & Engineering Chemistry Research, 45(9), 3001-3008. doi:10.1021/ie0512439.

Ma, Yun (2012) Chapter 3: Mechanistic Investigation of Nitroxide-based Polymerization Inhibitors. PhD thesis, University of York.

Niesbach, A., Daniels, J., Schröter, B., Lutze, P., & Górak, A. (2013). The inhibition of acrylic acid and acrylate ester polymerisation in a heterogeneously catalysed pilot-scale reactive distillation column. Chemical Engineering Science, 88, 95-107. doi:10.1016/j.ces.2012.10.029.

Okutsu, R., Ando, S., & Ueda, M. (2008). Sulfur-Containing Poly(meth)acrylates with High Refractive Indices and High Abbe's Numbers. Chemistry of Materials, 20(12), 4017-4023. doi:10.1021/cm800432p.

International Search Report and Written Opinion, PCT/IB2023/060631, dated Feb. 14, 2024, 11 pages.

International Search Report and Written Opinion, PCT/US2023/069730, dated Oct. 23, 2023, 12 pages.

International Search Report and Written Opinion, PCT/US2023/069702, dated Oct. 18, 2023, 16 pages.

Appelt, M. and Schmidt-Naake, G. "Stable Free-Radical Copolymerization of Styrene with Acrylates Using OH-TEMPO," Macromolecular Chemistry and Physics, 2004, vol. 205(6), pp. 637-644.

Bragd, P.L., Besemer, A.C., van Bekkum, H. "TEMPO-derivatives as catalysts in the oxidation of primary alcohol groups in carbohydrates," Journal of Molecular Catalysis A: Chemical, 2001, vol. 170(1-2), pp. 35-42.

Brinkmann-Rengel, S., N. Niessner. "Controlled Radical Copolymerization of Styrene and Acrylonitrile," American Cancer Society Symposium Series, chapter 28, vol. 768, Aug. 15, 2000, https://pubs.acs.org/doi/abs/10.1021/bk-2000-0768.ch02.

Edeleva, M.V., Marque, S.R., Bagryanskaya, E.G. "Imidazoline and imidazolidine nitroxides as controlling agents in nitroxide-mediated pseudoliving radical polymerization," Russian Chemical Reviews, Apr. 2018, vol. 87(4), pp. 328-349.

Edwards, B. A. "Comparing reducing agents in a pilot scale ClO2 generator: does hydrogen peroxide measure up?," Pulp & Paper Canada, 1996, vol. 97(5), pp. 34-37.

Georgieff, K.K. "Relative Inhibitory Effect of Various Compounds on the Rate of Polymerization of Methyl Methacrylate," Journal of Applied Polymer Science, 1965, vol. 9(6), pp. 2009-2018.

Goldfein, M.D., Gladyshev, G.P. "Kinetics and Mechanism of the Inhibited Polymerisation of Vinyl Monomers," Russian Chemical Reviews, 1988, vol. 57(11), p. 1083-1097.

Ichihara, K., Kawamura, I., Sakakibara, K. et al. "Inhibitory regulation mechanism of naphthoquinone and its derivatives in radical polymerization," Journal of Physical Organic Chemistry, 2019, vol. 32(6), pp. 1-11.

Kuznetsova, Y.L., Mozaleva, P.G., Vavilova, A.S., et al. "Polymerization of methyl methacrylate in the presence of 2,5-di-tert-butyl-p-benzoquinone," Russian Chemical Bulletin, Apr. 2020, vol. 69(4), pp. 763-767.

Ludin, D.V., Kuznetsova, Y.L., Zamyshlyaeva, O.G., Zaitsev, S.D. "Controlled Radical Copolymerization of Styrene and tert-Butyl Acrylate in the Presence of Tri-n-butylborane-p-Quinone Catalytic System," Polymer Science, Series B, 2017, vol. 59(1), pp. 7-15.

Naz, A., Sattar, R., Siddiq, M. "Polymer membranes for biofouling mitigation: a review," Polymer-Plastics Technology and Materials, 2019, vol. 58(17), pp. 1829-1854.

Pavlovskay, M.V., Smirnova, N.N., Markin, et al. "Synthesis of Block Copolymers from Polyvinyl Chloride Prepared in the Presence of Nitroxyl Radicals of the Imidazoline Series," Russian Journal of Applied Chemistry, 2014, vol. 87(3), pp. 324-330.

Rodriquez, B., Oztruk, D. et al. "Antibiofouling thin-film composite membranes (TFC) by in situ formation of Cu-(m-phenylenediamine) oligomer complex," Journal of Materials Science, Jan. 23, 2018, vol. 53, pp. 6325-6338.

(56) References Cited

OTHER PUBLICATIONS

Shushunova, N.Y., Arsenyev, M.V., Glukhova, T.A., et al. "Polymerization of Butyl Acrylate and Butyl Methacrylate in the Presence of o-Quinone Methacrylate," Polymer Science Series B, 2015, vol. 57(3), pp. 207-216.
Wang, Y., Meng X., Wu H., et al. "Improving permeability and anti-fouling performance in reverse osmosis application of polyamide thin film nanocomposite membrane modified with functionalized carbon nanospheres," Separation and Purification Technology, 2021, vol. 270, pp. 1-11.
Weng, S. and J. Zhang. "N-Oxyl-Radical-Catalyzed Intermolecular Aminooxygenation of Styrenes and Inter/intramolecular Aminoalkoxylation of Homoallylic Alcohols," ChemCatChem, 2016, vol. 8(24), pp. 3720-3724.
Yin, W., Chu, C., Lu, Q. et al. "Iron Chloride/4-Acetamido-TEMPO/Sodium Nitrite-Catalyzed Aerobic Oxidation of Primary Alcohols to the Aldehydes," Advanced Synthesis & Catalysis, 2010, vol. 352, pp. 113-118.
International Search Report and Written Opinion, PCT/US2020/026210, dated Jun. 17, 2020, 12 pages.
International Search Report and Written Opinion, PCT/US2023/065015, dated Jul. 17, 2023, 10 pages.
International Search Report and Written Opinion, PCT/US2023/065018, dated Jul. 7, 2023, 8 pages.
International Search Report and Written Opinion, PCT/US2023/065022, dated Jul. 26, 2023, 8 pages.
International Search Report and Written Opinion, PCT/US2023/065048, dated Jul. 14, 2023, 11 pages.
International Search Report and Written Opinion, PCT/US2023/065050, dated Jul. 7, 2023, 10 pages.

\* cited by examiner

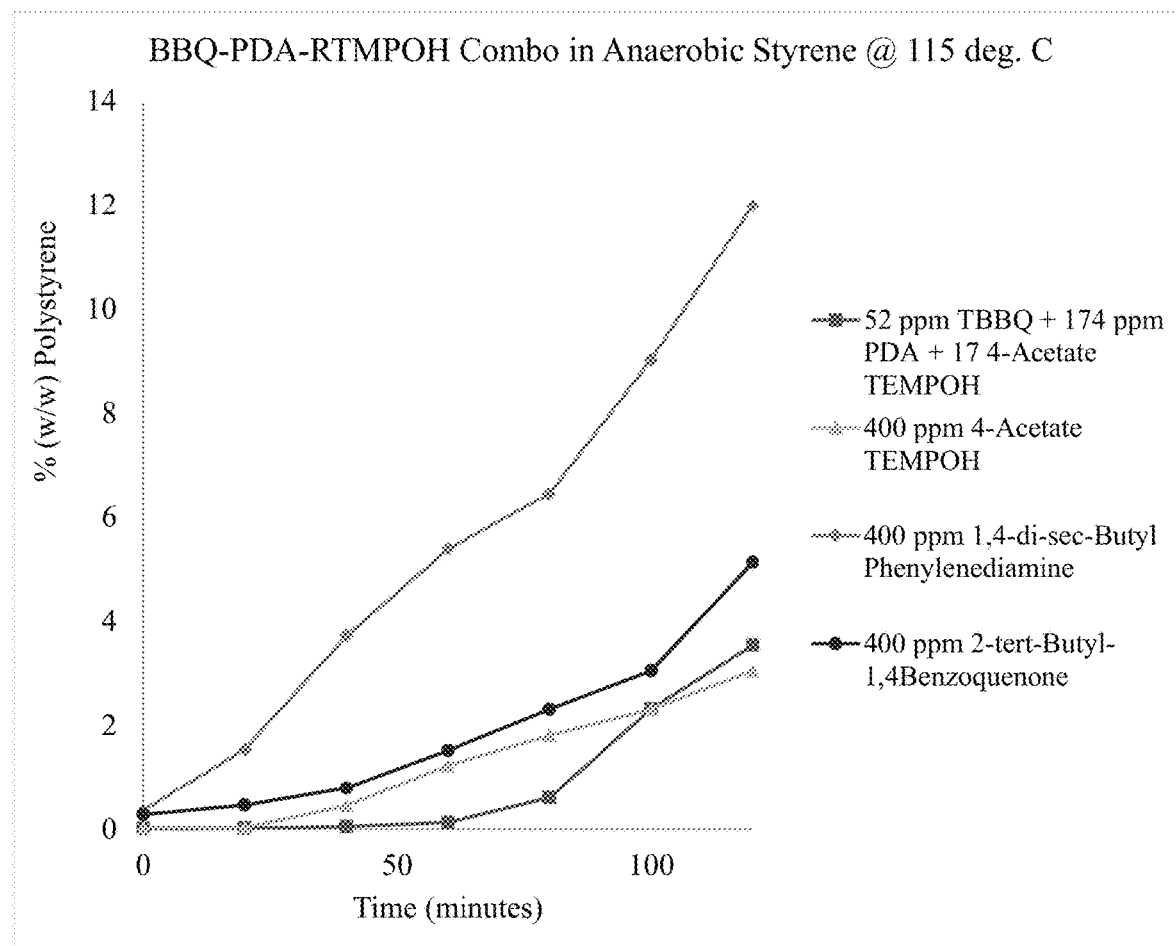

ANTIFOULANT COMPOSITIONS FOR VAPOR-SPACE APPLICATIONS

FIELD OF THE INVENTION

The present disclosure generally relates to compositions that include a blend of polymerization inhibitors and methods of using the same to inhibit unwanted polymerization in vapor-space areas. More particularly, the present disclosure relates to compositions that include at least one compound having a hydroxylamine of stable nitroxide radical, a quinone and a phenylenediamine, useful for inhibiting polymerization of ethylenic unsaturated monomers.

BACKGROUND

Ethylenically unsaturated monomers are typically manufactured in a three-stage process consisting of (i) reaction, (ii) recovery, and (iii) purification. Distillation operations at elevated temperatures are often involved in the recovery and purification stages. The processes include fractional distillation of the monomers. In the top sections of the distillation columns, purified monomer vapor condenses into liquid pools prior to transfer into storage facilities. Some of the condensed monomer streams cascade down the column. In the vapor space areas of the distillation column, the liquid monomer pools are likely to generate spontaneous or peroxide-initiated free-radicals. Current polymer inhibitor technologies are confined to liquid streams in the bottom sections of the process columns. The inhibitors are typically non-volatile so that they are confined to the bottom section of the distillation column, and no inhibitor reaches highly reactive monomer pools in the vapor-space sections. With conventional inhibitors, the pooled monomers are not treated to abate unwanted polymerization. For this reason, reactive monomers undesirably polymerize through radical polymerization especially at elevated temperature or when in contact with rust on the surfaces of the process equipment such as distillation column trays.

In the presence of polymerization initiators such as organic peroxides, which are ubiquitous in recycled streams previously exposed to atmospheric oxygen, this polymerization is particularly acute. Conventional polymerization inhibitors, such as 4-hydroxy-2,2,6,6-tetramethylpiperidin-1-oxyl (HTEMPO) and 4-oxo-2,2,6,6-tetramethylpiperidin-1-oxyl (OTEMPO) are generally effective. The premature polymerization of these monomers is generally controlled by directly dosing polymerization inhibitors into liquid hydrocarbon streams to reduce the premature polymerization of the monomers. However, these polymerization inhibitors (HTEMPO and OTEMPO) are not volatile. In the field, the process is accelerated when liquid monomer condenses on the trays, far above the bulk liquid that is treated with non-volatile polymerization inhibitors. The problem is acute if the trays have rust or when there are residual polymers in cracks and nooks. Equally important, preexisting polymers in equipment cracks, dead legs and stagnant pools of liquid monomer cause the rapid accumulation of foulant polymer due to the Norris-Trommsdorf effect. Due to accelerated polymerization, the growing polymer foulant causes mechanical damage and potential release of vast quantities of heat resulting in fires or explosions. The complete inhibition of tray corrosion or the complete removal of polymer from hard-to-reach locations in purification towers means that preventing unwanted polymerization in vapor spaces is difficult. It is in this regard that there is a pressing need for antipolymerants that are effective in the vapor-space sections of distillation columns.

BRIEF SUMMARY

A composition for inhibiting monomer polymerization is provided. The composition includes a first inhibitor compound comprising a hydroxylamine; a second inhibitor compound comprising a phenylenediamine; and a third inhibitor compound comprising a benzoquinone or naphthoquinone.

In some aspects, the first inhibitor compound is of formula (II):

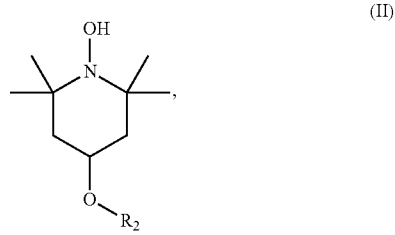

wherein $R_2$ is $C_1$-$C_{22}$ alkyl, $C_1$-$C_{22}$ alkenyl, $C_1$-$C_{22}$ alkynyl, $C_1$-$C_{22}$ cycloalkyl, aryl, —$C_1$-$C_{22}$ alkylene, —C(O)($C_1$-$C_{22}$ alkyl), —C(O)($C_1$-$C_{22}$ alkenyl), —C(O)($C_1$-$C_{22}$ alkynyl), —C(O)($C_1$-$C_{22}$ cycloalkyl), —C(O)(aryl), or —C(O)($C_1$-$C_{22}$ alkylene), wherein the alkyl, alkylene, cycloalkyl, and aryl are optionally substituted with one or more $C_1$-$C_{22}$ alkyl, $C_1$-$C_{22}$ alkenyl, $C_1$-$C_{22}$ alkynyl, or aryl.

In some aspects, $R_2$ is —C(O)($C_1$-$C_{22}$ alkyl), —C(O)($C_1$-$C_{22}$ alkenyl), —C(O)($C_1$-$C_{22}$ alkynyl), —C(O)($C_1$-$C_{22}$ cycloalkyl), —C(O)(aryl), or —C(O)($C_1$-$C_{22}$ alkylene), wherein the alkyl, alkylene, cycloalkyl, and aryl are optionally substituted with one or more $C_1$-$C_{22}$ alkyl, $C_1$-$C_{22}$ alkenyl, $C_1$-$C_{22}$ alkynyl, or aryl.

In some aspects, the first inhibitor is selected from the group consisting of: 2,2,6,6-tetramethylpiperin-1,4-diol; 4-methoxy-2,2,6,6-tetramethylpiperidin-1-ol; 4-ethoxy-2,2,6,6-tetramethylpiperidin-1-ol; 4-propoxy-2,2,6,6-tetramethylpiperidin-1-ol; 4-butoxy-2,2,6,6-tetramethylpiperidin-1-ol; 4-pentoxy-2,2,6,6-tetramethylpiperidin-1-ol; 4-hexyloxy-2,2,6,6-tetramethylpiperidin-1-ol; 4-heptyloxy-2,2,6,6-tetramethylpiperidin-1-ol; 4-octyloxy-2,2,6,6-tetramethylpiperidin-1-ol; 4-nonyloxy-2,2,6,6-tetramethylpiperidin-1-ol; 4-decyloxy-2,2,6,6-tetramethylpiperidin-1-ol; 4-undecyloxy-2,2,6,6-tetramethylpiperidin-1-ol; 4-dodecyloxy-2,2,6,6-tetramethylpiperidin-1-ol; 4-tridecyloxy-2,2,6,6-tetramethylpiperidin-1-ol; 4-tetradecyloxy-2,2,6,6-tetramethylpiperidin-1-ol; 4-pentadecyloxy-2,2,6,6-tetramethylpiperidin-1-ol; 4-hexadecyloxy-2,2,6,6-tetramethylpiperidin-1-ol; 4-heptadecyloxy-2,2,6,6-tetramethylpiperidin-1-ol; 4-octadecyloxy-2,2,6,6-tetramethylpiperidin-1-ol; 4-nodecyloxy-2,2,6,6-tetramethylpiperidin-1-ol; 4-decyloxy-2,2,6,6-tetramethylpiperidin-1-ol; 4-icosyloxy-2,2,6,6-tetramethylpiperidin-1-ol; 4-henicosyloxy-2,2,6,6-tetramethylpiperidin-1-ol; 4-docosyloxy-2,2,6,6-tetramethylpiperidin-1-ol; 4-(phenoxy)-2,2,6,6-tetramethylpiperidin-1-ol; 4-(benzyloxy)-2,2,6,6-tetramethylpiperidin-1-ol; 2,2,6,6-tetramethyl-4-(naphthalen-2-yloxy)piperidin-1-ol; and any combination thereof.

In some aspects, the first inhibitor is a compound of formula IIa:

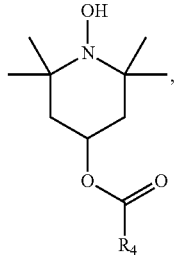

(IIa)

wherein $R_4$ is H, $C_1$-$C_{22}$ alkyl, $C_1$-$C_{22}$ alkenyl, $C_1$-$C_{22}$ alkynyl, $C_1$-$C_{22}$ cycloalkyl, aryl, —$C_1$-$C_{22}$ alkylene, —C(O)($C_1$-$C_{22}$ alkyl), —C(O)($C_1$-$C_{22}$ alkenyl), —C(O)($C_1$-$C_{22}$ alkynyl), —C(O)($C_1$-$C_{22}$ cycloalkyl), —C(O)(aryl), or —C(O)($C_1$-$C_{22}$ alkylene), wherein the alkyl, alkylene, cycloalkyl, and aryl are optionally substituted with one or more $C_1$-$C_{22}$ alkyl, $C_1$-$C_{22}$ alkenyl, $C_1$-$C_{22}$ alkynyl, or aryl.

In some aspects, the first inhibitor is selected from the group consisting of: 1-hydroxy-2,2,6,6-tetramethylpiperidin-4-yl acetate, 1-hydroxy-2,2,6,6-tetramethylpiperidin-4-yl propanoate, 1-hydroxy-2,2,6,6-tetramethylpiperidin-4-yl butyrate, 1-hydroxy-2,2,6,6-tetramethylpiperidin-4-yl pentanoate, 1-hydroxy-2,2,6,6-tetramethylpiperidin-4-yl hexanoate, 1-hydroxy-2,2,6,6-tetramethylpiperidin-4-yl heptanoate, 1-hydroxy-2,2,6,6-tetramethylpiperidin-4-yl octanoate, 1-hydroxy-2,2,6,6-tetramethylpiperidin-4-yl nonanoate, 1-hydroxy-2,2,6,6-tetramethylpiperidin-4-yl decanoate, 1-hydroxy-2,2,6,6-tetramethylpiperidin-4-ylundecanoate, 1-hydroxy-2,2,6,6-tetramethylpiperidin-4-yl dodecanoate, 1-hydroxy-2,2,6,6-tetramethylpiperidin-4-yl 2-ethylhexanoate, 1-hydroxy-2,2,6,6-tetramethylpiperidin-4-yl stearate, 1-hydroxy-2,2,6,6-tetramethylpiperidin-4-yl benzoate, 1-hydroxy-2,2,6,6-tetramethylpiperidin-4-yl palmitoate, 1-hydroxy-2,2,6,6-tetramethylpiperidin-4-yl behenoate, 1-hydroxy-2,2,6,6-tetramethylpiperidin-4-yl 4-tert-butylbenzoate, or any combination thereof.

In some aspects, the second inhibitor compound is a phenylenediamine of formula (IV) or formula (V):

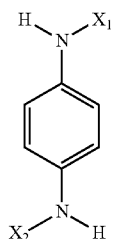

(IV)

para-phenylenediamine

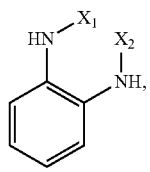

(V)

ortho-phenylenediamine wherein $X_1$ and $X_2$ are independently $C_1$-$C_{22}$ alkyl, or aryl, wherein the alkyl and aryl are optionally substituted with one or more $C_1$-$C_{22}$ alkyl or aryl.

In some aspects, the second inhibitor is selected from the group consisting of: 1,2-phenylenediamine, 1,4-phenylenediamine, N,N'-di-methyl-p-phenylenediamine, N,N'-di-sec-butyl-1,4-phenylenediamine, N,N'-di-1,4-dimethylpentyl-1,4-phenylenediamine, N,N'-di-ethyl-1,4-phenylenediamine, N-tert-butyl-N'-phenyl-1,4-phenylenediamine, N,N'-di-phenyl-1,4-phenylenediamine, and any combination thereof.

In some aspects, the third inhibitor compound is a benzoquinone of formula (VI) or formula (VII):

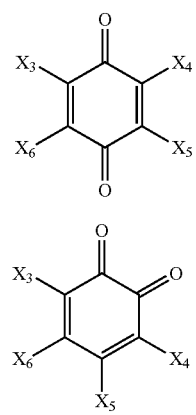

(VI)

(VII)

wherein $X_3$, $X_4$, $X_5$, and $X_6$ are independently H, $C_1$-$C_{22}$ alkyl, or aryl, wherein the alkyl and aryl are optionally substituted with one or more $C_1$-$C_{22}$ alkyl or aryl.

In some aspects, the third inhibitor compound is a naphthoquinone of formula (VII) or formula (VIII):

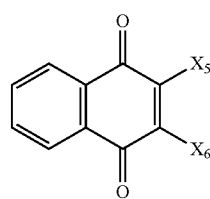

(VII)

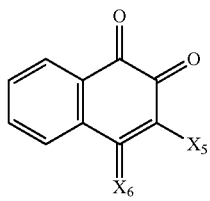

(VIII)

wherein $X_5$ and $X_6$ are independently H, $C_1$-$C_{22}$ alkyl, aryl, wherein the alkyl and aryl are optionally substituted with one or more $C_1$-$C_{22}$ alkyl or aryl.

In some aspects, the first inhibitor compound is present in the composition at a concentration of about 0.01% by weight to about 80% by weight, and the second inhibitor compound is present in the composition at a concentration of about 0.01% by weight to about 50% by weight.

In some aspects, the composition further comprises an organic solvent.

In some aspects, the composition further comprises an ethylenic unsaturated monomer selected from the group consisting of vinyl acetate, acrylonitrile, an acrylate, a methacrylate, 1,3-butadiene, styrene, isoprene, acrylic acid, methacrylic acid and any combination thereof.

A method of inhibiting polymerization of a monomer is provided. The method includes adding the composition described herein to the monomer.

In some aspects, the monomer is provided within a solution.

In some aspects, the solution further comprises one or more additional components selected from: an acid, an organic solvent, and water.

In some aspects, the monomer is an ethylenic unsaturated monomer.

In some aspects, the composition is added to the monomer such that a concentration of the first inhibitor compound is about 0.1 ppm to about 10,000 ppm.

In some aspects, the composition is added to the monomer such that a concentration of the second inhibitor compound is about 0.1 ppm to about 10,000 ppm.

In some aspects, the monomer is selected from the group consisting of vinyl acetate, acrylonitrile, an acrylate, a methacrylate, 1,3-butadiene, styrene, isoprene, acrylic acid, methacrylic acid and any combination thereof.

The foregoing has outlined rather broadly the features and technical advantages of the present disclosure in order that the detailed description that follows may be better understood. Additional features and advantages of the disclosure will be described hereinafter that form the subject of the claims of this application. It should be appreciated by those skilled in the art that the conception and the specific aspects disclosed may be readily utilized as a basis for modifying or designing other aspects for carrying out the same purposes of the present disclosure. It should also be realized by those skilled in the art that such equivalent aspects do not depart from the spirit and scope of the disclosure as set forth in the appended claims.

BRIEF DESCRIPTION OF THE DRAWINGS

A detailed description of the invention is hereafter described with specific reference being made to the drawings.

FIG. 1 shows kinetic curves showing the effectiveness of the combination of 4-Acetate TEMPO and N,N'-di-sec-butyl-1,4-phenylenediamine as an antipolymerant compared to the performance of a 25 ppm dose of composition of N,N'-di-sec-butyl-1,4-phenylenediamine and 2,6-di-tert-butylphenol for styrene polymerization at about 135° C. using the static method.

DETAILED DESCRIPTION

Various aspects of the present disclosure are described below. The relationship and functioning of the various elements of the aspects may better be understood by reference to the following detailed description. However, aspects are not limited to those explicitly described herein and it should be understood that, in certain instances, details may have been omitted that are not necessary for an understanding of the aspects disclosed herein, such as—for example—conventional synthesis and/or formulation.

The present disclosure relates to compositions that include a blend of polymerization inhibitors and methods of using the same to inhibit the polymerization of ethylenic unsaturated monomers. Polymerization inhibitor compositions of the present disclosure include a hydroxylamine, a phenylenediamine, and a benzoquinone or naphthoquinone.

A "polymerization inhibitor," in the presence of polymerizable monomers, inhibits the formation of a polymer from those monomers during the induction time. After the induction time has lapsed, the polymer's formation occurs at substantially the same rate that it would form at in the absence of the polymerization inhibitor.

Polymerization inhibitors and polymerization retarders can be considered generally as "antipolymerants" which are compounds that can inhibit or reduce the formation of polymers from one or more radically polymerizable compounds.

The term "fouling" refers to the formation of polymers, prepolymers, oligomer and/or other materials, which would become insoluble in and/or precipitate from a stream and deposit on equipment under the conditions of operation of the equipment. In turn, the inhibitor, retarder, and amine stabilizer components and compositions of the disclosure can be referred to as "antifouling" as they inhibit or reduce such formation.

Compositions of the Disclosure

The present disclosure relates to compositions for inhibiting monomer polymerization where the compositions include a first inhibitor compound includes a hydroxylamine, a second inhibitor compound comprising a phenylenediamine, and a third inhibitor compound comprising a benzoquinone or naphthoquinone. In some aspects, the compositions are for inhibiting monomer polymerization, where the monomer is an ethylenic unsaturated monomer. For example, the compositions of the disclosure are useful for inhibiting polymerization of ethylenic unsaturated monomers including, but not limited to, vinyl acetate, acrylonitrile, acrylates, methacrylates, 1,3-butadiene, styrene, isoprene, (meth)acrylic acid, and combinations thereof.

In some aspects, the first inhibitor compound is of formula (II):

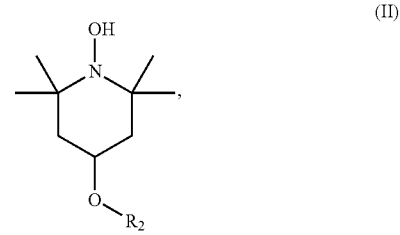

where $R_2$ is selected from H, $C_1$-$C_{22}$ alkyl, $C_1$-$C_{22}$ alkenyl, $C_1$-$C_{22}$ alkynyl, $C_1$-$C_{22}$ cycloalkyl, aryl, —$C_1$-$C_{22}$ alkylene, —C(O)($C_1$-$C_{22}$ alkyl), —C(O)($C_1$-$C_{22}$ alkenyl), —C(O)($C_1$-$C_{22}$ alkynyl), —C(O)($C_1$-$C_{22}$ cycloalkyl), —C(O)(aryl), and —C(O)($C_1$-$C_{22}$ alkylene), wherein the alkyl, alkylene, cycloalkyl, and aryl are optionally substituted with one or more $C_1$-$C_{22}$ alkyl, $C_1$-$C_{22}$ alkenyl, $C_1$-$C_{22}$ alkynyl, or aryl.

The term "aryl" refers to monocyclic, bicyclic (fused), and tricyclic (fused or spiro) hydrocarbon ring systems having a total of five to fourteen ring carbon atoms, wherein at least one ring in the system is aromatic and wherein each ring in the system contains 3 to 7 ring carbon atoms. The term "aryl" may be used interchangeably with the term "aryl ring."

In certain aspects, $R_2$ is —C(O)($C_1$-$C_{22}$ alkyl), —C(O)($C_1$-$C_{22}$ alkenyl), —C(O)($C_1$-$C_{22}$ alkynyl), —C(O)($C_1$-$C_{22}$ cycloalkyl), —C(O)(aryl), and —C(O)($C_1$-$C_{22}$ alkylene), where the alkyl, alkylene, cycloalkyl, and aryl are optionally substituted with one or more $C_1$-$C_{22}$ alkyl, $C_1$-$C_{22}$ alkenyl, $C_1$-$C_{22}$ alkynyl, or aryl.

In some aspects, $R_2$ is H. In some aspects, $R_2$ is $C_1$-$C_{22}$ alkyl. In some aspects, $R_2$ is $C_1$-$C_{22}$ alkenyl. In some aspects, $R_2$ is $C_1$-$C_{22}$ alkynyl. In some aspects, $R_2$ is $C_1$-$C_{22}$ cycloalkyl, where the cycloalkyl is optionally substituted with one or more $C_1$-$C_{22}$ alkyl, $C_1$-$C_{22}$ alkenyl, $C_1$-$C_{22}$ alkynyl, or aryl. In some aspects, $R_2$ is aryl, where the aryl is optionally substituted with one or more $C_1$-$C_{22}$ alkyl, $C_1$-$C_{22}$ alkenyl, $C_1$-$C_{22}$ alkynyl, or aryl. In some aspects, $R_2$ is —$C_1$-$C_{22}$ alkylene, where the alkylene is optionally substituted with aryl that is optionally substituted with one or more $C_1$-$C_{22}$ alkyl, $C_1$-$C_{22}$ alkenyl, $C_1$-$C_{22}$ alkynyl, or aryl. In some aspects, $R_2$ is —C(O)($C_1$-$C_{22}$ alkyl). In some aspects, $R_2$ is —C(O)($C_1$-$C_{12}$ alkyl). In some aspects, $R_2$ is —C(O)($C_1$-$C_6$ alkyl). In some aspects, $R_2$ is —C(O)(methyl). In some aspects, $R_2$ is —C(O)(ethyl). In some aspects, $R_2$ is —C(O)(propyl). In some aspects, $R_2$ is —C(O)(butyl). In some aspects, $R_2$ is —C(O)($C_1$-$C_{22}$ alkenyl). In some aspects, $R_2$ is —C(O)($C_1$-$C_{22}$ alkynyl). In some aspects, $R_2$ is —C(O)($C_1$-$C_{22}$ cycloalkyl), where the cycloalkyl is optionally substituted with one or more $C_1$-$C_{22}$ alkyl, $C_1$-$C_{22}$ alkenyl, $C_1$-$C_{22}$ alkynyl, or aryl. In some aspects, $R_2$ is —C(O)(aryl), where the aryl is optionally substituted with one or more $C_1$-$C_{22}$ alkyl, $C_1$-$C_{22}$ alkenyl, $C_1$-$C_{22}$ alkynyl, or aryl. In some aspects, $R_2$ is —C(O)($C_1$-$C_{22}$ alkylene), where the alkylene is optionally substituted with aryl that is optionally substituted with one or more $C_1$-$C_{22}$ alkyl, $C_1$-$C_{22}$ alkenyl, $C_1$-$C_{22}$ alkynyl, or aryl.

In some aspects, the compound of formula (II) is 2,2,6,6-tetramethylpiperin-1,4-diol; 4-methoxy-2,2,6,6-tetramethylpiperidin-1-ol; 4-ethoxy-2,2,6,6-tetramethylpiperidin-1-ol; 4-propoxy-2,2,6,6-tetramethylpiperidin-1-ol; 4-butoxy-2,2,6,6-tetramethylpiperidin-1-ol; 4-pentoxy-2,2,6,6-tetramethylpiperidin-1-ol; 4-hexyloxy-2,2,6,6-tetramethylpiperidin-1-ol; 4-heptyloxy-2,2,6,6-tetramethylpiperidin-1-ol; 4-octyloxy-2,2,6,6-tetramethylpiperidin-1-ol; 4-nonyloxy-2,2,6,6-tetramethylpiperidin-1-ol; 4-decyloxy-2,2,6,6-tetramethylpiperidin-1-ol; 4-undecyloxy-2,2,6,6-tetramethylpiperidin-1-ol; 4-dodecyloxy-2,2,6,6-tetramethylpiperidin-1-ol; 4-tridecyloxy-2,2,6,6-tetramethylpiperidin-1-ol; 4-tetradecyloxy-2,2,6,6-tetramethylpiperidin-1-ol; 4-pentadecyloxy-2,2,6,6-tetramethylpiperidin-1-ol; 4-hexadecyloxy-2,2,6,6-tetramethylpiperidin-1-ol; 4-heptadecyloxy-2,2,6,6-tetramethylpiperidin-1-ol; 4-octadecyloxy-2,2,6,6-tetramethylpiperidin-1-ol; 4-nodecyloxy-2,2,6,6-tetramethylpiperidin-1-ol; 4-decyloxy-2,2,6,6-tetramethylpiperidin-1-ol; 4-icosyloxy-2,2,6,6-tetramethylpiperidin-1-ol; 4-henicosyloxy-2,2,6,6-tetramethylpiperidin-1-ol; 4-docosyloxy-2,2,6,6-tetramethylpiperidin-1-ol; 4-(phenoxy)-2,2,6,6-tetramethylpiperidin-1-ol; 4-(benzyloxy)-2,2,6,6-tetramethylpiperidin-1-ol; or 2,2,6,6-tetramethyl-4-(naphthalen-2-yloxy)piperidin-1-ol.

In certain aspects, the compositions of the disclosure include compounds of formula (I) and (II), respectively, where $R_1$ and $R_2$ are the same. For example, in some aspects, the compositions of the disclosure include compounds of formula (I) and (II), respectively, where $R_1$ and $R_2$ are each, independently, —C(O)($C_1$-$C_{22}$ alkyl). In certain aspects, the compositions of the disclosure include first and second inhibitor compounds of formula (I) and (II), respectively, where $R_1$ and $R_2$ are different.

In some aspects, the second inhibitor compound having a hydroxylamine is selected from the group consisting of:

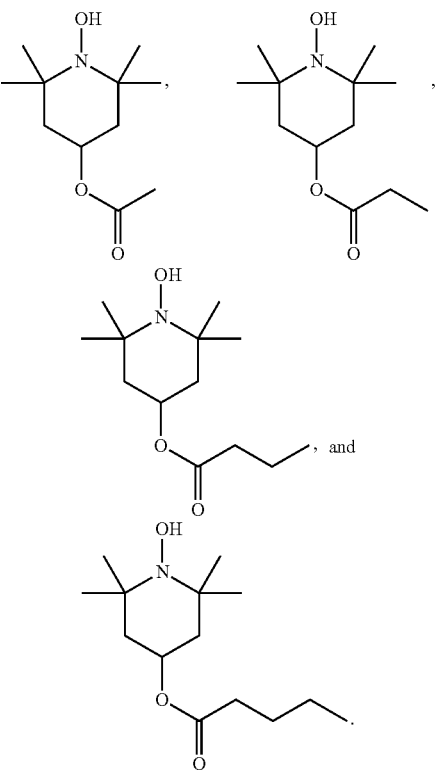

In some aspects, the second inhibitor compound having a hydroxylamine is:

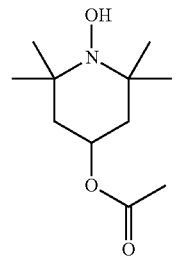

4-acetoxy-2,2,6,6-tetramethylpiperidin-1-ol.

In some aspects, the second inhibitor compound having a hydroxylamine is:

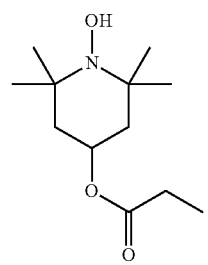 [SMILES: CCC(=O)OC1CC(C)(C)N(O)C(C)(C)C1]

4-propionoxy-2,2,6,6-tetramethylpiperidin-1-ol.

In some aspects, the second inhibitor compound having a hydroxylamine is:

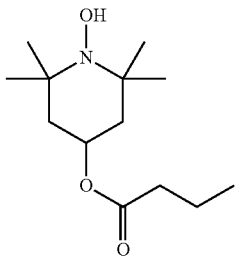 [SMILES: CCCC(=O)OC1CC(C)(C)N(O)C(C)(C)C1]

4-butyroxy-2,2,6,6-tetramethylpiperidin-1-ol.

In some aspects, the second inhibitor compound having a hydroxylamine is:

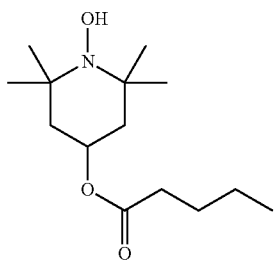 [SMILES: CCCCC(=O)OC1CC(C)(C)N(O)C(C)(C)C1]

4-valeroxy-2,2,6,6-tetramethylpiperidin-1-ol.

The presently disclosed compound of formula (II) having a hydroxylamine has benefits over the corresponding nitroxide (compound of formula (I)), such as the capability to provide additional polymerization inhibition, as will be more fully explained below. A general synthetic route to produce a hydroxylamine of a nitroxide is to reduce its corresponding nitroxide with a reducing reagent as follows:

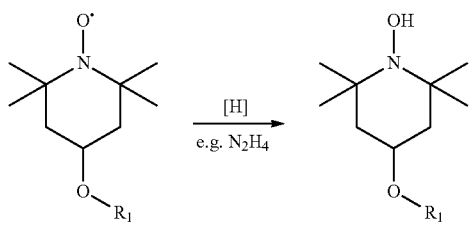

A hydroxylamine of a nitroxide has the potential to provide additional polymerization inhibition as compared to the corresponding nitroxide when carbon-centered and oxygen-centered radical initiators are present. This is explained as follows:

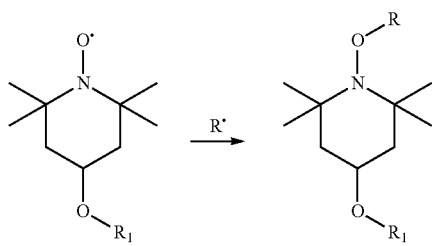

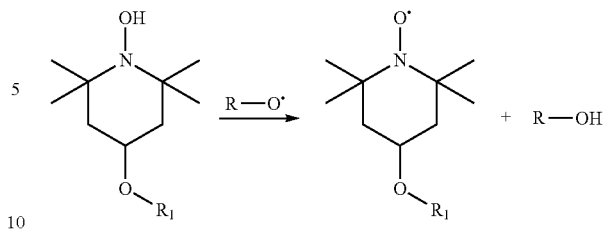

The hydroxylamine of a nitroxide is an excellent hydrogen donor due to its weak NO—H bond in the compound, and thus it is an efficient antioxidant. As an antioxidant, the hydroxylamine of a nitroxide easily reacts with oxygen-centered radicals, such as peroxide radicals, while it's converted to its corresponding nitroxide. Nitroxides are generally known as the most effective inhibitors because of their superior inhibiting capabilities through scavenging carbon-centered free radicals at a nearly diffusion controlled rate. This rate is several orders of magnitude faster than phenolic compounds. However, their kinetic superiority is not always advantageous. For instance, it may lose its superiority when oxygen-centered radicals are present as the predominant free radicals. Another issue of concern with a nitroxide is its consumption through non-inhibition and unwanted reactions with process stream components or other inhibitor additives. As a result, high nitroxide inhibitor dosages are often required for a given inhibition efficacy, thereby making their use economically unattractive or even infeasible.

In essence, each hydroxylamine of a nitroxide is equivalent to one hydrogen donor plus one nitroxide antipolymerant when oxygen-centered radicals and carbon-centered radicals are both present, which is an attractive incentive offered by the hydroxylamines of nitroxides. That is, one hydroxylamine of a nitroxide is able to eliminate one oxygen-centered radical and one carbon-centered radical whereas a nitroxide is only capable to eliminate a carbon-centered radical.

In some aspects, the first inhibitor is a compound of formula IIa:

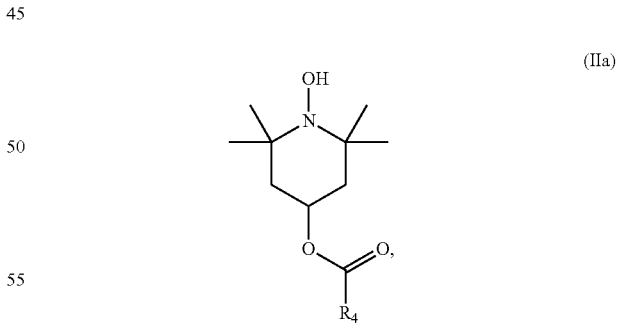

wherein $R_4$ is H, $C_1$-$C_{22}$ alkyl, $C_1$-$C_{22}$ alkenyl, $C_1$-$C_{22}$ alkynyl, $C_1$-$C_{22}$ cycloalkyl, aryl, —$C_1$-$C_{22}$ alkylene, —C(O)($C_1$-$C_{22}$ alkyl), —C(O)($C_1$-$C_{22}$ alkenyl), —C(O)($C_1$-$C_{22}$ alkynyl), —C(O)($C_1$-$C_{22}$ cycloalkyl), —C(O)(aryl), or —C(O)($C_1$-$C_{22}$ alkylene), wherein the alkyl, alkylene, cycloalkyl, and aryl are optionally substituted with one or more $C_1$-$C_{22}$ alkyl, $C_1$-$C_{22}$ alkenyl, $C_1$-$C_{22}$ alkynyl, or aryl.

In some aspects, the first inhibitor is a compound of formula III:

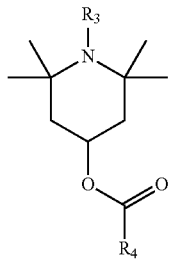

(III)

wherein $R_3$ is —O· or —OH; and $R_4$ is $C_1$-$C_{22}$ alkyl or aryl, wherein the alkyl and aryl are optionally substituted with one or more $C_1$-$C_{22}$ alkyl or aryl.

In some aspects, $R_3$ is —O·. In some aspects, $R_3$ is —OH.

In some aspects with regard to formulae (IIa) and (III), $R_4$ is $C_1$-$C_{22}$ alkyl that is optionally substituted with one or more $C_1$-$C_{22}$ alkyl or aryl. In some aspects with regard to formulae (IIa) and (III), $R_4$ is $C_1$-$C_5$ alkyl that is optionally substituted with one or more $C_1$-$C_{22}$ alkyl or aryl. In some aspects with regard to formulae (IIa) and (III), $R_4$ is $C_1$-$C_4$ alkyl that is optionally substituted with one or more $C_1$-$C_{22}$ alkyl or aryl. In some aspects with regard to formulae (IIa) and (III), $R_4$ is $C_1$-$C_{10}$ alkyl that is optionally substituted with one or more $C_1$-$C_{22}$ alkyl or aryl. In some aspects with regard to formulae (IIa) and (III), $R_4$ is $C_1$—C alkyl that is optionally substituted with one or more $C_1$-$C_{22}$ alkyl or aryl. In some aspects, $R_4$ is aryl that is optionally substituted with one or more $C_1$-$C_{22}$ alkyl or aryl. In some aspects, $R_4$ is methyl. In some aspects, $R_4$ is propyl. In some aspects, $R_4$ is butyl. In some aspects, $R_4$ is a $C_5$ alkyl group. In some aspects, $R_4$ is a $C_6$ alkyl group. In some aspects, $R_4$ is a $C_7$ alkyl group. In some aspects, $R_4$ is a $C_8$ alkyl group. In some aspects, $R_9$ is a $C_5$ alkyl group. In some aspects, $R_4$ is a $C_{10}$ alkyl group. In some aspects, $R_4$ is a $C_{22}$ alkyl group. In some aspects, $R_4$ is a $C_{21}$ alkyl group. In some aspects, $R_4$ is a $C_{11}$ alkyl group. In some aspects, $R_4$ is a benzyl group.

Examples of a compound of formulae (IIa) or (III) include, but are not limited to, 1-oxyl-2,2,6,6-tetramethylpiperidin-4-yl acetate; 1-oxyl-2,2,6,6-tetramethylpiperidin-4-yl propanoate; 1-oxyl-2,2,6,6-tetramethylpiperidin-4-yl butyrate; 1-oxyl-2,2,6,6-tetramethylpiperidin-4-yl pentanoate; 1-oxyl-2,2,6,6-tetramethylpiperidin-4-yl hexanoate; 1-oxyl-2,2,6,6-tetramethylpiperidin-4-yl heptanoate; 1-oxyl-2,2,6,6-tetramethylpiperidin-4-yl octanoate; 1-oxyl-2,2,6,6-tetramethylpiperidin-4-yl nonanoate; 1-oxyl-2,2,6,6-tetramethylpiperidin-4-yl decanoate; 1-oxyl-2,2,6,6-tetramethylpiperidin-4-yl undecanoate; 1-oxyl-2,2,6,6-tetramethylpiperidin-4-yl dodecanoate; 1-oxyl-2,2,6,6-tetramethylpiperidin-4-yl 2-ethylhexanoate; 1-oxyl-2,2,6,6-tetramethylpiperidin-4-yl stearate; 1-oxyl-2,2,6,6-tetramethylpiperidin-4-yl benzoate; 1-oxyl-2,2,6,6-tetramethylpiperidin-4-yl palmitoate; 1-oxyl-2,2,6,6-tetramethylpiperidin-4-yl behenoate; or 1-oxyl-2,2,6,6-tetramethylpiperidin-4-yl 4-tert-butylbenzoate.

In some aspects, the compound of formulae (IIa) or (III) is 1-oxyl-2,2,6,6-tetramethylpiperidin-4-yl acetate; 1-oxyl-2,2,6,6-tetramethylpiperidin-4-yl propanoate; or 1-oxyl-2,2,6,6-tetramethylpiperidin-4-yl butyrate. In some aspects, the compound of formulae (IIa) or (III) is 1-oxyl-2,2,6,6-tetramethylpiperidin-4-yl acetate. In some aspects, the compound of formulae (IIa) or (III) is 1-oxyl-2,2,6,6-tetramethylpiperidin-4-yl propanoate. In some aspects, the compound of formulae (IIa) or (III) is 1-oxyl-2,2,6,6-tetramethylpiperidin-4-yl butyrate.

In some aspects, the second inhibitor compound is a phenylenediamine of formula (IV) or formula (V):

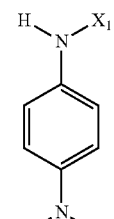

(IV)

para-phenylenediamine

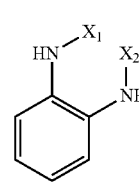

(V)

ortho-phenylenediamine wherein $X_1$ and $X_2$ are independently $C_1$-$C_{22}$ alkyl, or aryl, wherein the alkyl and aryl are optionally substituted with one or more $C_1$-$C_{22}$ alkyl or aryl.

In some aspects, the second inhibitor compound is a phenylenediamine of formula (IV). In some aspects, the second inhibitor compound is a phenylenediamine of formula (V).

Examples of phenylenediamines include, but are not limited to, 1,2-phenylenediamine, 1,4-phenylenediamine, N,N'-di-methyl-p-phenylenediamine, N,N'-di-sec-butyl-1,4-phenylenediamine, N,N'-di-1,4-dimethylpentyl-1,4-phenylenediamine, N,N'-di-ethyl-1,4-phenylenediamine, N-tert-butyl-N'-phenyl-1,4-phenylenediamine, and N,N'-di-phenyl-1,4-phenylenediamine.

In some aspects, the phenylenediamine is N,N'-di-sec-butyl-1,4-phenylenediamine, N,N'-di-1,4-dimethylpentyl-1,4-phenylenediamine, N,N'-di-ethyl-1,4-phenylenediamine, N-tert-butyl-N'-phenyl-1,4-phenylenediamine, or N,N'-di-phenyl-1,4-phenylenediamine.

In some aspects, the phenylenediamine is N,N'-di-sec-butyl-1,4-phenylenediamine.

In some aspects, the phenylenediamine is N,N'-di-1,4-dimethylpentyl-1,4-phenylenediamine.

In some aspects, the phenylenediamine is N,N'-di-ethyl-1,4-phenylenediamine.

In some aspects, the phenylenediamine is N-tert-butyl-N'-phenyl-1,4-phenylenediamine.

In some aspects, the phenylenediamine is N,N'-di-phenyl-1,4-phenylenediamine.

In some aspects, the third inhibitor compound is a benzoquinone of formula (VI) or formula (VII):

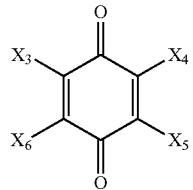

(VI)

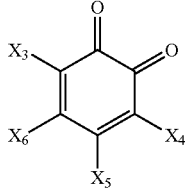

(VII)

wherein $X_3$, $X_4$, $X_5$, and $X_6$ are independently H, $C_1$-$C_{22}$ alkyl, or aryl, wherein the alkyl and aryl are optionally substituted with one or more $C_1$-$C_{22}$ alkyl or aryl.

In some aspects, the third inhibitor compound is a benzoquinone of formula (VI). In some aspects, the third inhibitor compound is a benzoquinone of formula (VII).

In some aspects, the third inhibitor compound is a naphthoquinone of formula (VII) or formula (VIII):

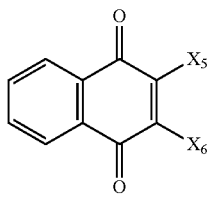

(VII)

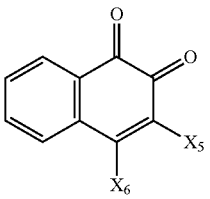

(VIII)

wherein $X_5$ and $X_6$ are independently H, $C_1$-$C_{22}$ alkyl, aryl, wherein the alkyl and aryl are optionally substituted with one or more $C_1$-$C_{22}$ alkyl or aryl.

In some aspects, $X_5$ and $X_6$ are independently H or $C_1$-$C_{22}$ alkyl.

In some aspects, $X_5$ and $X_6$ are independently H or $C_1$-$C_{15}$ alkyl.

In some aspects, $X_5$ and $X_6$ are independently H or $C_1$-$C_{10}$ alkyl.

In some aspects, $X_5$ and $X_6$ are independently H or $C_1$-$C_5$ alkyl.

In some aspects, the third inhibitor compound is a naphthoquinone of formula (VII). In some aspects, the third inhibitor compound is a naphthoquinone of formula (VIII).

In some aspects, $X_3$, $X_4$, $X_5$, and $X_6$ are independently H or $C_1$-$C_{22}$ alkyl. In some aspects, at least one of $X_3$, $X_4$, $X_5$, and $X_6$ is $C_1$-$C_{22}$ alkyl. In some aspects, $X_3$, $X_4$, and $X_5$ are H and $X_6$ is $C_1$-$C_{22}$ alkyl. In some aspects, $X_3$, $X_4$, and $X_5$ are H and $X_6$ is $C_1$-$C_{10}$ alkyl. In some aspects, $X_3$, $X_4$, and $X_5$ are H and $X_6$ is tert-butyl.

Examples of benzoquinones include, but are not limited to, 2-tert-butyl-1,4-benzoquinone, 2-tert-butyl-5-methylbenzoquinone, 2-sec-butyl-5-methylbenzoquinone, 2-n-butyl-5-methylbenzoquinone, 2-sec-butyl-5-methylbenzoquinone, 2-iso-propyl-5-methylbenzoquinone, 2,5-di-sec-butylbenzoquinone, 2,5-di-tert-butylbenzoquinone, 2,5-di-iso-popylbenzoquinone, 2,6-di-sec-butylbenzoquinone, 2,6-di-tert-butylbenzoquinone, 2,6-di-iso-popylbenzoquinone, 2,6-di-methylbenzoquinone, 2,5-di-methylbenzoquinone, 2,6-di-ethylbenzoquinone, 2,5-di-ethylbenzoquinone, 2,6-di-proylbenzoquinone, 2,5-di-propylbenzoquinone, 2,6-di-n-butylbenzoquinone, 2,5-di-n-buylbenzoquinone, 2,6-di-tert-butylbenzoquinone, 2,6-di-iso-propylbenzoquinone, 2-n-pentylbenzoquinone, 2,6-di-n-pentylbenzoquinone, 2,6-di-n-pentylbenzoquinone, 2-n-hexylbenzoquinone, 2,6-di-hexylbenzoquinone, 2,6-di-hexylbenzoquinone, 2-n-heptylbenzoquinone, 2,6-di-heptylbenzoquinone, 2,6-di-heptylbenzoquinone, 2-n-octylbenzoquinone, 2,6-di-octylbenzoquinone, 2,6-di-octylbenzoquinone, 2-n-nonylbenzoquinone, 2,6-di-nonylbenzoquinone, 2,6-di-nonylbenzoquinone, 2-n-decylbenzoquinone, 2,6-di-decylbenzoquinone, 2,6-di-decylbenzoquinone, 2-n-undecylbenzoquinone, 2,6-di-undecylbenzoquinone, 2,6-di-undecylbenzoquinone, 2-n-dodecylbenzoquinone, 2,6-di-dodecylbenzoquinone, and 2,6-di-dodecylbenzoquinone In some aspects, the benzoquinone is 2-tert-butyl-1,4-benzoquinone.

Examples of naphthoquinones include, but are not limited to, 1,4-naphthoquinone, 1,2-naphthoquinone, 1-methyl-1,4-naphthoquinone, 1-ethyl-1,4-naphthoquinone, 1-n-propyl-1,4-naphthoquinone, 1-isopropyl-1,4-naphthoquinone, 1-n-butyl-1,4-naphthoquinone, 1-sec-butyl-1,4-naphthoquinone, 1-tert-butyl-1,4-naphthoquinone, 1-methyl-1,2-naphthoquinone, 1-ethyl-1,2-naphthoquinone, 1-n-propyl-1,2-naphthoquinone, 1-isopropyl-1,2-naphthoquinone, 1-n-butyl-1,2-naphthoquinone, 1-sec-butyl-1,2-naphthoquinone, and 1-tert-butyl-1,2-naphthoquinone In some aspects, the composition consists essentially of a first inhibitor compound, a second inhibitor compound, and a third inhibitor compound. In other aspects, the composition consists of an organic solvent, a first inhibitor, a second inhibitor, and a third inhibitor compound. In some aspects, the composition does not include 4-hydroxy-2,2,6,6-tetramethylpiperidin-1-oxyl.

In some aspects, the first inhibitor compound is present in the composition at a concentration of about 0.01% by weight to about 80% by weight. In some aspects, the first inhibitor compound is present in the composition at a concentration of about 0.01% by weight to about 70% by weight. In some aspects, the first inhibitor compound is present in the composition at a concentration of about 0.01% by weight to about 60% by weight. In some aspects, the first inhibitor compound is present in the composition at a concentration of about 0.01% by weight to about 50% by weight. In some aspects, the first inhibitor compound is present in the composition at a concentration of about 0.01% by weight to about 40% by weight. In some aspects, the first inhibitor compound is present in the composition at a concentration of about 0.01% by weight to about 30% by weight. In some aspects, the first inhibitor compound is present in the composition at a concentration of about 0.01% by weight to about 20% by weight. In some aspects, the first inhibitor compound is present in the composition at a concentration of about 0.01% by weight to about 10% by weight.

For example, in certain aspects, the first inhibitor compound is present in the composition at a concentration of about 0.01% by weight, about 0.1% by weight, about 1% by weight, about 5% by weight, about 10% by weight, about 15% by weight, about 20% by weight, about 25% by weight, about 30% by weight, about 35% by weight, about 40% by weight, about 45% by weight, about 50% by weight, about 55% by weight, about 60% by weight, about 65% by weight, about 70% by weight, about 75% by weight, or about 80% by weight.

In some aspects, the second inhibitor compound is present in the composition at a concentration of about 0.01% by weight to about 50% by weight. In some aspects, the second inhibitor compound is present in the composition at a concentration of about 0.01% by weight to about 40% by weight. In some aspects, the second inhibitor compound is present in the composition at a concentration of about 0.01% by weight to about 30% by weight. In some aspects, the second inhibitor compound is present in the composition at a concentration of about 0.01% by weight to about 20% by weight. In some aspects, the second inhibitor compound is present in the composition at a concentration of about 0.01% by weight to about 10% by weight.

For example, in certain aspects, the second inhibitor compound is present in the composition at a concentration of about 0.01% by weight, about 0.1% by weight, about 1% by weight, about 5% by weight, about 10% by weight, about 15% by weight, about 20% by weight, about 25% by weight, about 30% by weight, about 35% by weight, about 40% by weight, about 45% by weight, or about 50% by weight.

In some aspects, the third inhibitor compound is present in the composition at a concentration of about 0.01% by weight to about 80% by weight. In some aspects, the third inhibitor compound is present in the composition at a concentration of about 0.01% by weight to about 70% by weight. In some aspects, the third inhibitor compound is present in the composition at a concentration of about 0.01% by weight to about 60% by weight. In some aspects, the third inhibitor compound is present in the composition at a concentration of about 0.01% by weight to about 50% by weight. In some aspects, the third inhibitor compound is present in the composition at a concentration of about 0.01% by weight to about 40% by weight. In some aspects, the third inhibitor compound is present in the composition at a concentration of about 0.01% by weight to about 30% by weight. In some aspects, the third inhibitor compound is present in the composition at a concentration of about 0.01% by weight to about 20% by weight. In some aspects, the third inhibitor compound is present in the composition at a concentration of about 0.01% by weight to about 10% by weight.

For example, in certain aspects, the third inhibitor compound is present in the composition at a concentration of about 0.01% by weight, about 0.1% by weight, about 1% by weight, about 5% by weight, about 10% by weight, about 15% by weight, about 20% by weight, about 25% by weight, about 30% by weight, about 35% by weight, about 40% by weight, about 45% by weight, about 50% by weight, about 55% by weight, about 60% by weight, about 65% by weight, about 70% by weight, about 75% by weight, or about 80% by weight.

In some aspects, a mole ratio of the first inhibitor compound to the second inhibitor compound is about 100:1 to about 1:100. In some aspects, a mole ratio of the first inhibitor compound to the second inhibitor compound is about 90:1 to about 1:90. In some aspects, a mole ratio of the first inhibitor compound to the second inhibitor compound is about 80:1 to about 1:80. In some aspects, a mole ratio of the first inhibitor compound to the second inhibitor compound is about 70:1 to about 1:70. In some aspects, a mole ratio of the first inhibitor compound to the second inhibitor compound is about 60:1 to about 1:60. In some aspects, a mole ratio of the first inhibitor compound to the second inhibitor compound is about 50:1 to about 1:50. In some aspects, a mole ratio of the first inhibitor compound to the second inhibitor compound is about 40:1 to about 1:40. In some aspects, a mole ratio of the first inhibitor compound to the second inhibitor compound is about 30:1 to about 1:30. In some aspects, a mole ratio of the first inhibitor compound to the second inhibitor compound is about 20:1 to about 1:20. In some aspects, a mole ratio of the first inhibitor compound to the second inhibitor compound is about 10:1 to about 1:10. In some aspects, a mole ratio of the first inhibitor compound to the second inhibitor compound is about 1:1.

In some aspects, the composition also includes one or more additional compounds selected from the group consisting of 2,2,6,6-tetramethylpiperidin-1-oxyl; 2,2,6,6-tetramethylpiperidin-1-ol; 4-hydroxyl-2,2,6,6-tetramethylpiperidin-1-oxyl; 4-hydroxy-2,2,6,6-tetramethylpiperidin-1-ol; 4-oxo-2,2,6,6-tetramethylpiperidin-1-oxyl; 4-oxo-2,2,6,6-tetramethylpiperidin-1-ol; 4-acetoxy-2,2,6,6-tetramethylpiperidin-1-oxyl; 4-acetoxy-2,2,6,6-tetramethylpiperidin-1-ol; 4-propionoxy-2,2,6,6-tetramethylpiperidin-1-oxyl; 4-propionoxy-2,2,6,6-tetramethylpiperidin-1-ol; and bis((2,2,6,6-tetramethylpiperidin-1-oxyl)-4-yl) oxalate. In some aspects, the composition also includes 2,2,6,6-tetramethylpiperidin-1-oxyl. In some aspects, the composition also includes 2,2,6,6-tetramethylpiperidin-1-ol. In some aspects, the composition also includes 4-hydroxyl-2,2,6,6-tetramethylpiperidin-1-oxyl. In some aspects, the composition also includes 4-hydroxy-2,2,6,6-tetramethylpiperidin-1-ol. In some aspects, the composition also includes 4-oxo-2,2,6,6-tetramethylpiperidin-1-oxyl. In some aspects, the composition also includes 4-oxo-2,2,6,6-tetramethylpiperidin-1-ol. In some aspects, the composition also includes 4-acetoxy-2,2,6,6-tetramethylpiperidin-1-oxyl. In some aspects, the composition also includes 4-acetoxy-2,2,6,6-tetramethylpiperidin-1-ol. In some aspects, the composition also includes 4-propionoxy-2,2,6,6-tetramethylpiperidin-1-oxyl. In some aspects, the composition also includes 4-propionoxy-2,2,6,6-tetramethylpiperidin-1-ol. In some aspects, the composition also includes bis((2,2,6,6-tetramethylpiperidin-1-oxyl)-4-yl) oxalate.

The composition may optionally also include one or more organic solvents. One of ordinary skill in the art will appreciate that there are many organic solvents that are compatible with the compositions of the disclosure. For example, in some aspects, the one or more organic solvents are selected from vinyl acetate, dimethyl phthalate, dimethylformamide, toluene, xylene, highly aromatic naphtha, acetonitrile, ethyl acetate, acetone, dichloromethane, tetrahydrofuran, hexanes, dimethyl sulfoxide, N-methyl-2-pyrrolidone, and combinations thereof. In certain aspects, the composition also includes vinyl acetate. In certain aspects, the composition also includes dimethyl phthalate. In certain aspects, the composition also includes dimethylformamide. In certain aspects, the composition also includes toluene. In certain aspects, the composition also includes xylene. In certain aspects, the composition also includes highly aromatic naphtha. In certain aspects, the composition also includes acetonitrile.

In some aspects, the composition also includes one or more ethylenic unsaturated monomers. One of ordinary skill in the art will appreciate that there are many ethylenic unsaturated monomers that are compatible with the compositions of the disclosure. For example, in some aspects, the one or more ethylenic unsaturated monomers are selected from vinyl acetate, acrylonitrile, acrylate esters, methacrylate esters, 1,3-butadiene, styrene, isoprene, (meth)acrylic acid, and combinations thereof. In certain aspects, the composition also includes vinyl acetate. In certain aspects, the composition also includes acrylonitrile. In certain aspects, the composition also includes acrylates. In certain aspects, the composition also includes methacrylates. In certain aspects, the composition also includes 1,3-butadiene. In certain aspects, the composition also includes styrene. In certain aspects, the composition also includes isoprene. In certain aspects, the composition also includes acrylic acid and (meth)acrylic acid.

Methods of Using the Compositions of the Disclosure

The present disclosure also relates to methods of inhibiting polymerization of monomers that include adding a composition of the disclosure to the monomer. In some aspects, an effective amount of the composition of the disclosure is added to the monomer, where an effective amount is any amount sufficient to inhibit the polymerization of the monomer.

In some aspects, the monomer is an ethylenic unsaturated monomer. In some aspects the monomer is an ethylenic unsaturated monomer selected from vinyl acetate, acrylonitrile, acrylate esters, methacrylate esters, 1,3-butadiene, styrene, isoprene, (meth)acrylic acid, and combinations thereof are disclosed. In some aspects, the methods disclosed herein are useful in inhibiting the polymerization of vinyl acetate. In some aspects, the methods disclosed herein are useful in inhibiting the polymerization of acrylonitrile. In some aspects, the methods disclosed herein are useful in inhibiting the polymerization of acrylates. In some aspects, the methods disclosed herein are useful in inhibiting the polymerization of methacrylates. In some aspects, the methods disclosed herein are useful in inhibiting the polymerization of 1,3-butadiene. In some aspects, the methods disclosed herein are useful in inhibiting the polymerization of styrene. In some aspects, the methods disclosed herein are useful in inhibiting the polymerization of isoprene. In some aspects, the methods disclosed herein are useful in inhibiting the polymerization of (meth)acrylic acid.

The composition of the disclosure can be added manually or automatically to the fluid. The composition can also be added continuously and/or intermittently. Automatic addition may be accomplished through the use of chemical injection pumps. The chemical injection pumps may be programmed to add particular amounts of the polymerization inhibitor composition, or any components thereof, at certain time intervals to the fluid. In alternate aspects, the chemical injection pumps can be manually controlled to add particular amounts of the polymerization inhibitor composition, or any components thereof, to the fluid. Addition of the presently disclosed polymerization inhibitor compositions to the monomer will thereby inhibit polymerization of the monomer.

In some aspects, the monomer is provided as a neat liquid. In other aspects, the monomer is provided within a solution, hereafter referred to as "the monomer solution."

In some aspects, the monomer solution also includes one or more additional components selected from an acid, an organic solvent, water, and combinations thereof. For example, in some aspects, the monomer solution includes one or more organic solvents selected from vinyl acetate, dimethyl phthalate, dimethylformamide, toluene, xylene, highly aromatic naphtha, acetonitrile, ethyl acetate, acetone, dichloromethane, tetrahydrofuran, hexanes, dimethyl sulfoxide, N-methyl-2-pyrrolidone, and combinations thereof.

In some aspects, the composition is added to the monomer such that a concentration of the first inhibitor compound is about 0.1 ppm to about 10,000 ppm. In some aspects, the composition is added to the monomer such that a concentration of the first inhibitor compound is about 0.1 ppm to about 5,000 ppm. In some aspects, the composition is added to the monomer such that a concentration of the first inhibitor compound is about 0.1 ppm to about 1,000 ppm. In some aspects, the composition is added to the monomer such that a concentration of the first inhibitor compound is about 0.1 ppm to about 500 ppm.

In some aspects, the composition is added to the monomer such that a concentration of the second inhibitor compound is about 0.1 ppm to about 10,000 ppm. In some aspects, the composition is added to the monomer such that a concentration of the second inhibitor compound is about 0.1 ppm to about 5,000 ppm. In some aspects, the composition is added to the monomer such that a concentration of the second inhibitor compound is about 0.1 ppm to about 1,000 ppm. In some aspects, the composition is added to the monomer such that a concentration of the second inhibitor compound is about 0.1 ppm to about 500 ppm.

In some aspects, the composition is added to the monomer such that a concentration of the third inhibitor compound is about 0.1 ppm to about 10,000 ppm. In some aspects, the composition is added to the monomer such that a concentration of the third inhibitor compound is about 0.1 ppm to about 5,000 ppm. In some aspects, the composition is added to the monomer such that a concentration of the third inhibitor compound is about 0.1 ppm to about 1,000 ppm. In some aspects, the composition is added to the monomer such that a concentration of the third inhibitor compound is about 0.1 ppm to about 500 ppm.

The methods of the disclosure are useful for inhibiting the premature polymerization of monomers during manufacturing process, particularly those that are performed under acidic conditions. For example, the methods of the disclosure are useful for preventing polymerization of acrylates, which may include, but are not limited to, acrylonitrile, acrylic acid, methyl methacrylic acid and its esters, and vinyl acetate.

The methods of the disclosure are also useful for preventing the premature polymerization of styrene during manufacturing and purification processes.

The methods of the disclosure are also useful in butadiene extraction processes. This utility stems from the balanced partition coefficients between polar organic phases and organic phases.

In some aspects, the compositions disclosed herein are used in distillative purification of olefins. For example, the composition can be added to the process stream before entering the distillation unit or the composition can be added to the process stream in the distillation unit.

EXAMPLES

Example 1—Polymerization Inhibition with N,N-di-sec-butylphenylenediamine (PDA)

The ability of compositions of the disclosure to inhibit the polymerization of polystyrene was assessed via the following protocol. Styrene was used as the reactive monomer for the polymerization kinetics studies and screening of the proposed antipolymerant products. To prevent polymerization during storage and transportation, styrene is stabilized with tert-butylcatechol (TBC). For each run of experiments, the stabilizer was removed, and the styrene thus freshly cleaned was used immediately. Styrene was used as the reactive monomer for the polymerization kinetics studies and screening of the proposed antipolymerant products. To prevent polymerization during storage and transportation, styrene is stabilized with TBC. For each run of experiments, the stabilizer was removed, and the styrene thus freshly cleaned was used immediately.

As a precaution, styrene that was cleaned and stored overnight, even under sub-zero refrigeration conditions, had to be discarded, since there was notable polymerization under storage. Alumina was used to remove the TBC using a chromatography column. The alumina column was prepared on the day of the scheduled set of experiments.

Into a 500 mL round bottom flask, about 300 mL of neat styrene treated with about 400 ppm of N,N-di-sec-butylphenylenediamine, the prototype PDA, were charged. A thermocouple was inserted directly into the reaction solution and the reaction temperature of the solution set for 115° C. To prevent the loss of the reaction solution due to evaporation, the flask was armed with a reflux equipment before being placed on a heating block. Through another port, a stream of nitrogen was flowed through the reaction solution while under vigorous stirring during the course of the kinetics study. The moment in time when the solution temperature reached 115° C. was designated as the beginning of the study, or time zero. A sample of the reaction solution was taken from the reactor after which the solution was immediately diluted with toluene. The concentration of polystyrene in the diluted solution was analyze using a proprietary procedure. From that point in time, a sample was collected every 20 minutes and the reaction solution similarly diluted and analyzed for the concentration of polystyrene.

Example 2—Polymerization Inhibition with 4-Acetoxy TEMPOH

The polymerization reactor was charged with 300 mL of styrene freshly cleaned and treated with 400 ppm of 4-Acetoxy TEMPOH. The reaction kinetics study was conducted as illustrated in Example 1.

Example 3—Polymerization Inhibition with 2-tert-Butylbenzoquinone

Using the procedure in the above examples, the antipolymerant performance of 400 ppm of 2-tert-butylbenzoquinone was carried out.

Example 4—Polymerization Inhibition with a Synergistic Composition of 2-tert-Butylbenzoquinone, 4-Acetoxy TEMPOH and PDA A freshly prepared solution of styrene, 300 mL, was treated with 52 ppm of TBBQ, 174 ppm of PDA and 174 ppm of 4-Acetoxy TEMPOH. The solution was transferred into polymerization reactor followed by the kinetics study using the procedure in the foregoing examples.

The samples tested and the results of the assay are shown in FIG. 1 and summarized in Table 1 below.

TABLE 1

Percent (w/w) concentration of polystyrene under anaerobic conditions.

| Time | 400 ppm 4-acetate TEMPOH | 400 ppm PDA | 400 ppm TBBQ | 52 ppm TBBQ + 174 ppm PDA + 174-Acetate TEMPOH |
|---|---|---|---|---|
| 0 | 0.0213 | 0.362 | 0.279 | 0.00825 |
| 20 | 0.0266 | 1.54 | 0.461 | 0.0183 |
| 40 | 0.450 | 3.72 | 0.794 | 0.0480 |
| 60 | 1.23 | 5.38 | 1.52 | 0.128 |
| 80 | 1.81 | 6.45 | 2.31 | 0.605 |
| 100 | 2.31 | 9.03 | 3.05 | 2.32 |
| 120 | 3.05 | 12.0 | 5.13 | 3.54 |

All of the compositions and methods disclosed and claimed herein can be made and executed without undue experimentation in light of the present disclosure. While this invention may be embodied in many different forms, there are described in detail herein specific preferred aspects of the invention. The present disclosure is an exemplification of the principles of the invention and is not intended to limit the invention to the particular aspects illustrated. In addition, unless expressly stated to the contrary, use of the term "a" is intended to include "at least one" or "one or more." For example, "a compound" is intended to include "at least one compound" or "one or more compounds."

Any ranges given either in absolute terms or in approximate terms are intended to encompass both, and any definitions used herein are intended to be clarifying and not limiting. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges (including all fractional and whole values) subsumed therein.

Any composition disclosed herein may comprise, consist of, or consist essentially of any element, component and/or ingredient disclosed herein or any combination of two or more of the elements, components or ingredients disclosed herein.

Any method disclosed herein may comprise, consist of, or consist essentially of any method step disclosed herein or any combination of two or more of the method steps disclosed herein.

The transitional phrase "comprising," which is synonymous with "including," "containing," or "characterized by," is inclusive or open-ended and does not exclude additional, un-recited elements, components, ingredients and/or method steps.

The transitional phrase "consisting of" excludes any element, component, ingredient, and/or method step not specified in the claim.

The transitional phrase "consisting essentially of" limits the scope of a claim to the specified elements, components, ingredients and/or steps, as well as those that do not materially affect the basic and novel characteristic(s) of the claimed invention.

As used herein, the term "about" refers to the cited value being within the errors arising from the standard deviation found in their respective testing measurements, and if those errors cannot be determined, then "about" may refer to, for example, within 5% of the cited value.

Furthermore, the invention encompasses any and all possible combinations of some or all of the various aspects described herein. It should also be understood that various changes and modifications to the presently preferred aspects described herein will be apparent to those skilled in the art. Such changes and modifications can be made without departing from the spirit and scope of the invention and without diminishing its intended advantages. It is therefore intended that such changes and modifications be covered by the appended claims.

What is claimed is:

1. A composition for inhibiting monomer polymerization consisting essentially of:
   a first inhibitor compound comprising a hydroxylamine;
   a second inhibitor compound comprising a phenylenediamine; and
   a third inhibitor compound comprising a benzoquinone or naphthoquinone.

2. The composition of claim 1, wherein the first inhibitor compound is of formula (II):

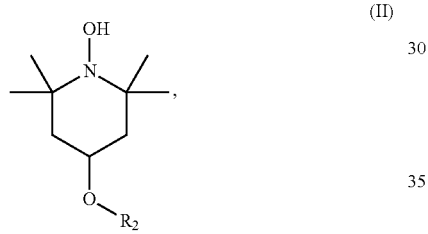

(II)

wherein $R_2$ is $C_1$-$C_{22}$ alkyl, $C_1$-$C_{22}$ alkenyl, $C_1$-$C_{22}$ alkynyl, $C_1$-$C_{22}$ cycloalkyl, aryl, —$C_1$-$C_{22}$ alkylene, —C(O)($C_1$-$C_{22}$ alkyl), —C(O)($C_1$-$C_{22}$ alkenyl), —C(O)($C_1$-$C_{22}$ alkynyl), —C(O)($C_1$-$C_{22}$ cycloalkyl), —C(O)(aryl), or —C(O)($C_1$-$C_{22}$ alkylene), wherein the alkyl, alkylene, cycloalkyl, and aryl are optionally substituted with one or more $C_1$-$C_{22}$ alkyl, $C_1$-$C_{22}$ alkenyl, $C_1$-$C_{22}$ alkynyl, or aryl.

3. The composition of claim 1, wherein $R_2$ is —C(O)($C_1$-$C_{22}$ alkyl), —C(O)($C_1$-$C_{22}$ alkenyl), —C(O)($C_1$-$C_{22}$ alkynyl), —C(O)($C_1$-$C_{22}$ cycloalkyl), —C(O)(aryl), or —C(O)($C_1$-$C_{22}$ alkylene), wherein the alkyl, alkylene, cycloalkyl, and aryl are optionally substituted with one or more $C_1$-$C_{22}$ alkyl, $C_1$-$C_{22}$ alkenyl, $C_1$-$C_{22}$ alkynyl, or aryl.

4. The composition of claim 1, wherein the first inhibitor is selected from the group consisting of: 2,2,6,6-tetramethylpiperin-1,4-diol; 4-methoxy-2,2,6,6-tetramethylpiperidin-1-ol; 4-ethoxy-2,2,6,6-tetramethylpiperidin-1-ol; 4-propoxy-2,2,6,6-tetramethylpiperidin-1-ol; 4-butoxy-2,2,6,6-tetramethylpiperidin-1-ol; 4-pentoxy-2,2,6,6-tetramethylpiperidin-1-ol; 4-hexyloxy-2,2,6,6-tetramethylpiperidin-1-ol; 4-heptyloxy-2,2,6,6-tetramethylpiperidin-1-ol; 4-octyloxy-2,2,6,6-tetramethylpiperidin-1-ol; 4-nonyloxy-2,2,6,6-tetramethylpiperidin-1-ol; 4-decyloxy-2,2,6,6-tetramethylpiperidin-1-ol; 4-undecyloxy-2,2,6,6-tetramethylpiperidin-1-ol; 4-dodecyloxy-2,2,6,6-tetramethylpiperidin-1-ol; 4-tridecyloxy-2,2,6,6-tetramethylpiperidin-1-ol; 4-tetradecyloxy-2,2,6,6-tetramethylpiperidin-1-ol; 4-pentadecyloxy-2,2,6,6-tetramethylpiperidin-1-ol; 4-hexadecyloxy-2,2,6,6-tetramethylpiperidin-1-ol; 4-heptadecyloxy-2,2,6,6-tetramethylpiperidin-1-ol; 4-octadecyloxy-2,2,6,6-tetramethylpiperidin-1-ol; 4-nodecyloxy-2,2,6,6-tetramethylpiperidin-1-ol; 4-decyloxy-2,2,6,6-tetramethylpiperidin-1-ol; 4-icosyloxy-2,2,6,6-tetramethylpiperidin-1-ol; 4-henicosyloxy-2,2,6,6-tetramethylpiperidin-1-ol; 4-docosyloxy-2,2,6,6-tetramethylpiperidin-1-ol; 4-(phenoxy)-2,2,6,6-tetramethylpiperidin-1-ol; 4-(benzyloxy)-2,2,6,6-tetramethylpiperidin-1-ol; 2,2,6,6-tetramethyl-4-(naphthalen-2-yloxy)piperidin-1-ol; and any combination thereof.

5. The composition of claim 1, wherein the first inhibitor is a compound of formula IIa:

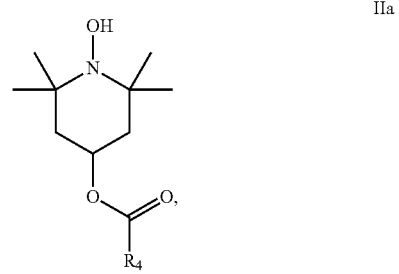

IIa wherein $R_4$ is H, $C_1$-$C_{22}$ alkyl, $C_1$-$C_{22}$ alkenyl, $C_1$-$C_{22}$ alkynyl, $C_1$-$C_{22}$ cycloalkyl, aryl, —$C_1$-$C_{22}$ alkylene, —C(O)($C_1$-$C_{22}$ alkyl), —C(O)($C_1$-$C_{22}$ alkenyl), —C(O)($C_1$-$C_{22}$ alkynyl), —C(O)($C_1$-$C_{22}$ cycloalkyl), —C(O)(aryl), or —C(O)($C_1$-$C_{22}$ alkylene), wherein the alkyl, alkylene, cycloalkyl, and aryl are optionally substituted with one or more $C_1$-$C_{22}$ alkyl, $C_1$-$C_{22}$ alkenyl, $C_1$-$C_{22}$ alkynyl, or aryl.

6. The composition of claim 5, wherein the first inhibitor is selected from the group consisting of: 1-hydroxy-2,2,6,6-tetramethylpiperidin-4-yl acetate, 1-hydroxy-2,2,6,6-tetramethylpiperidin-4-yl propanoate, 1-hydroxy-2,2,6,6-tetramethylpiperidin-4-yl butyrate, 1-hydroxy-2,2,6,6-tetramethylpiperidin-4-yl pentanoate, 1-hydroxy-2,2,6,6-tetramethylpiperidin-4-yl hexanoate, 1-hydroxy-2,2,6,6-tetramethylpiperidin-4-yl heptanoate, 1-hydroxy-2,2,6,6-tetramethylpiperidin-4-yl octanoate, 1-hydroxy-2,2,6,6-tetramethylpiperidin-4-yl nonanoate, 1-hydroxy-2,2,6,6-tetramethylpiperidin-4-yl decanoate, 1-hydroxy-2,2,6,6-tetramethylpiperidin-4-ylundecanoate, 1-hydroxy-2,2,6,6-tetramethylpiperidin-4-yl dodecanoate, 1-hydroxy-2,2,6,6-tetramethylpiperidin-4-yl 2-ethylhexanoate, 1-hydroxy-2,2,6,6-tetramethylpiperidin-4-yl stearate, 1-hydroxy-2,2,6,6-tetramethylpiperidin-4-yl benzoate, 1-hydroxy-2,2,6,6-tetramethylpiperidin-4-yl palmitoate, 1-hydroxy-2,2,6,6-tetramethylpiperidin-4-yl behenoate, 1-hydroxy-2,2,6,6-tetramethylpiperidin-4-yl 4-tert-butylbenzoate, or any combination thereof.

7. The composition of claim 1, wherein the second inhibitor compound is a phenylenediamine of formula (IV) or formula (V):

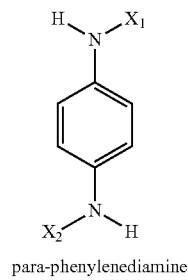

para-phenylenediamine (IV)

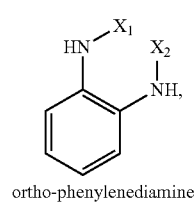

ortho-phenylenediamine (V)

wherein $X_1$ and $X_2$ are independently $C_1$-$C_{22}$ alkyl, or aryl, wherein the alkyl and aryl are optionally substituted with one or more $C_1$-$C_{22}$ alkyl or aryl.

8. The composition of claim 1, wherein the second inhibitor is selected from the group consisting of: 1,2-phenylenediamine, 1,4-phenylenediamine, N,N'-di-methyl-p-phenylenediamine, N,N'-di-sec-butyl-1,4-phenylenediamine, N,N'-di-1,4-dimethylpentyl-1,4-phenylenediamine, N,N'-di-ethyl-1,4-phenylenediamine, N-tert-butyl-N'-phenyl-1,4-phenylenediamine, N,N'-di-phenyl-1,4-phenylenediamine, and any combination thereof.

9. The composition of claim 1, wherein the third inhibitor compound is a benzoquinone of formula (VI) or formula (VII):

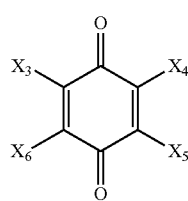

(VI)

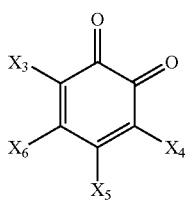

(VII)

wherein $X_3$, $X_4$, $X_5$, and $X_6$ are independently H, $C_1$-$C_{22}$ alkyl, or aryl, wherein the alkyl and aryl are optionally substituted with one or more $C_1$-$C_{22}$ alkyl or aryl.

10. The composition of claim 1, wherein the third inhibitor compound is a naphthoquinone of formula (VII) or formula (VIII):

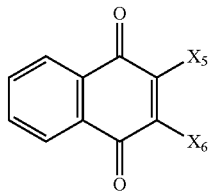

(VII)

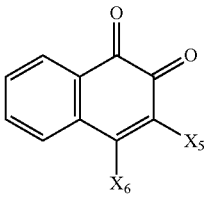

(VIII)

wherein $X_5$ and $X_6$ are independently H, $C_1$-$C_{22}$ alkyl, aryl, wherein the alkyl and aryl are optionally substituted with one or more $C_1$-$C_{22}$ alkyl or aryl.

11. The composition of claim 1, wherein the first inhibitor compound is present in the composition at a concentration of about 0.01% by weight to about 80% by weight, and the second inhibitor compound is present in the composition at a concentration of about 0.01% by weight to about 50% by weight.

12. The composition of claim 1, wherein the composition further comprises an organic solvent.

13. The composition of claim 1, wherein the composition further comprises an ethylenic unsaturated monomer selected from the group consisting of vinyl acetate, acrylonitrile, an acrylate, a methacrylate, 1,3-butadiene, styrene, isoprene, acrylic acid, methacrylic acid and any combination thereof.

14. A method of inhibiting polymerization of a monomer, the method comprising:
adding the composition of claim 1 to the monomer.

15. The method of claim 14, wherein the monomer is provided within a solution.

16. The method of claim 15, wherein the solution further comprises one or more additional components selected from: an acid, an organic solvent, and water.

17. The method of claim 14, wherein the monomer is an ethylenic unsaturated monomer.

18. The method of claim 14, wherein the composition is added to the monomer such that a concentration of the first inhibitor compound is about 0.1 ppm to about 10,000 ppm.

19. The method of claim 14, wherein the composition is added to the monomer such that a concentration of the second inhibitor compound is about 0.1 ppm to about 10,000 ppm.

* * * * *